US008632526B2

(12) United States Patent
Brownell et al.

(10) Patent No.: US 8,632,526 B2
(45) Date of Patent: Jan. 21, 2014

(54) SYSTEM AND METHOD OF INTERFACING A SURGICAL LASER WITH AN EYE (75) Inventors: Michael Brownell, San Clemente, CA (US); Ferenc Raksi, Irvine, CA (US)

(73) Assignee: AMO Development, LLC, Santa Ana, CA (US)

( * ) Notice: Subject to any disclaimer, the term of this patent is extended or adjusted under 35 U.S.C. 154(b) by 1785 days.

(21) Appl. No.: 11/936,714

(22) Filed: Nov. 7, 2007

(65) Prior Publication Data
US 2009/0118717 A1 May 7, 2009

(51) Int. Cl.
*A61B 18/20* (2006.01)
(52) U.S. Cl.
USPC .................................. 606/4; 606/10; 351/208
(58) Field of Classification Search
USPC .......... 606/4–6, 10–13, 16–18; 351/205–212; 607/88, 89; 128/898
See application file for complete search history.

(56) References Cited

U.S. PATENT DOCUMENTS

| 2004/0070761 | A1 | 4/2004 | Horvath et al. | |
| 2005/0192562 | A1* | 9/2005 | Loesel et al. | 606/5 |
| 2007/0173791 | A1* | 7/2007 | Raksi | 606/4 |

FOREIGN PATENT DOCUMENTS

| EP | 1970034 A1 | 9/2008 |
| WO | 2006090217 A1 | 8/2006 |

* cited by examiner

*Primary Examiner* — Ahmed Farah
(74) *Attorney, Agent, or Firm* — AMO Development, LLC (57) ABSTRACT

A system for interfacing a surgical laser with an eye includes a first sensing element to couple to an output surface of the laser, an interface lens having second sensing element coupled to a first surface of the interface lens, and a detector coupled to the first sensing element. A second surface of the interface lens contacts the eye. The detector determines when the first sensing element contacts the second sensing element. A method for aligning the laser with the eye includes coupling the laser to the patient interface, sensing an electrical change indicating a position of the output surface with the interface lens, comparing the electrical change with a predetermined value to produce a correction, and re-positioning the laser with the correction.

8 Claims, 5 Drawing Sheets

SYSTEM AND METHOD OF INTERFACING A SURGICAL LASER WITH AN EYE

BACKGROUND OF THE INVENTION

1. Field of the Invention

The field of the present invention is generally related to patient interface systems and, more particularly, to ophthalmic interface apparatus and system and method for interfacing surgical lasers with an eye.

2. Background

Lasers are being used more and more frequently in certain ophthalmic surgical procedures. For example, an ophthalmic surgical laser may be utilized to remove cataracts, re-shape the cornea, or the like. An accurate positioning of the eye in relationship to the laser allows the laser beam to be directed with a high degree of accuracy. Patient interface devices have been constructed to stabilize the eye in relation to the laser and typically have a corneal interface end and an attachment end for coupling to the laser. The corneal interface end is temporarily secured to a patient's cornea, and then the laser is docked to the attachment end to subsequently provide therapy. The corneal interface end typically uses a clear interface lens to contact the cornea. This patient interface device is suited to stabilizing the eye and providing a fixed reference for alignment of the laser with the patient's eye.

The relative position of the interface lens with respect to the output surface of the surgical laser may affect the alignment of the laser with the patient's eye (e.g., along at least one of an x-axis, a y-axis, a z-axis, a tilt, a rotation, or the like). For proper alignment of the eye relative to the surgical laser, the physical dimension tolerances of the patient interface device components may be maintained at a high degree of precision. For example, precise machining of the components may improve this alignment. However, with multiple parts in the patient interface assembly, the cumulative tolerance may contribute a significant error.

Accordingly, it is desirable to provide a system and a method for interfacing a surgical laser with an eye that determines and minimizes alignment errors between the surgical laser and the eye. It is also desirable to provide a system and method for interfacing a surgical laser with an eye, using a patient interface device, that determines the presence and position between the surgical laser output and the patient interface device. Additionally, other desirable features and characteristics of the present invention will become apparent from the subsequent detailed description and the appended claims, taken in conjunction with the accompanying drawings and the foregoing technical field and background.

SUMMARY OF THE INVENTION

Systems and methods are provided for interfacing a surgical laser with an eye. In one embodiment, system is provided for interfacing a surgical laser with an eye. The system includes a first sensing element configured to couple to an output surface of the surgical laser, an interface lens having a first surface and a second surface, and a detector coupled to the first sensing element. The first surface of the interface lens is configured to contact the eye. The interface lens includes a second sensing element coupled to the second surface of the interface lens. The detector is configured to determine when the first sensing element contacts the second sensing element.

In another embodiment, a surgical system for an eye is provided including a laser having an output surface, and a patient interface having a first end and a second end. The output surface comprises a first sensing element. The first end of the patient interface is configured to couple to the laser, and the second end is configured to couple to the eye. The patient interface includes an interface lens having a first surface and a second surface, and a second sensing element coupled to the second surface of the interface lens. The first surface of the interface lens is configured to contact the eye. The laser is operable to couple the output surface with the second surface of the interface lens.

In yet another embodiment, a method for aligning a surgical laser with a patient interface is provided including coupling the surgical laser to the patient interface, sensing an electrical change associated with the first sensing element, comparing the electrical change with a predetermined value to produce a correction, and re-positioning the surgical laser with the correction. The electrical change indicates a position of an output surface of the surgical laser with the interface lens.

BRIEF DESCRIPTION OF THE DRAWINGS

One or more exemplary embodiments of the present invention will hereinafter be described in conjunction with the following drawings, wherein like reference numerals denote like components.

DETAILED DESCRIPTION

Systems and methods are provided for interfacing an ophthalmic surgical laser with an eye. In general, the laser couples to the eye via a patient interface device having an interface lens for contacting the cornea. One example of a patient interface device is described in U.S. patent application Ser. No. 11/258,399, filed Oct. 24, 2005, the disclosure of which is incorporated herein by reference, although other patient interface devices may be utilized with one or more of the exemplary embodiments. These systems and methods utilize one or more sensing elements with the output surface of the laser (e.g., the output surface of the laser head) to determine when the laser contacts the interface lens and the relative position of the laser with the interface lens. This position may then be used to make corrections to the position of the laser to align the laser with the patient interface device and thus with the eye.

Figure 1:
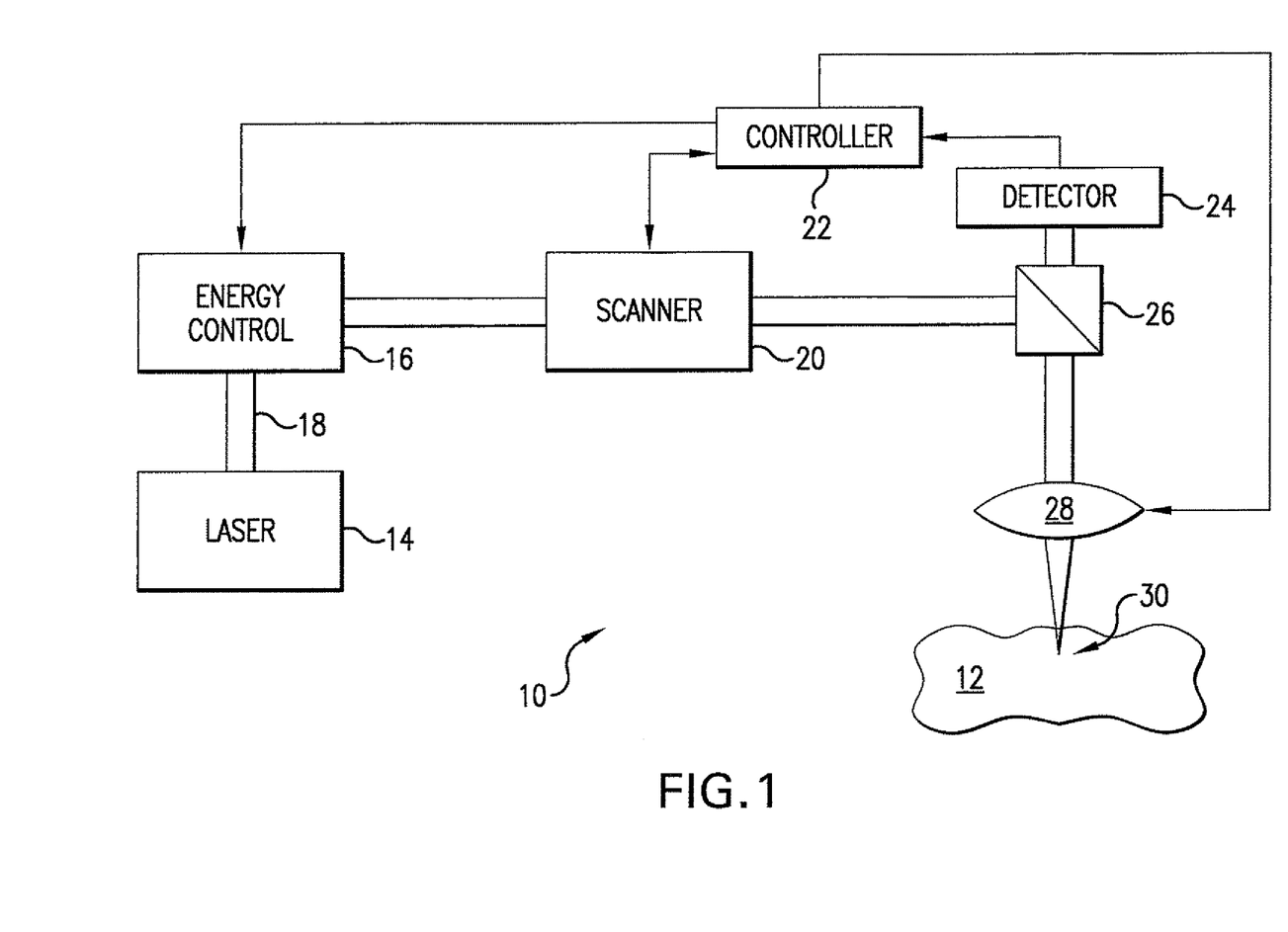
FIG. 1 is a block diagram of a laser scanner system in accordance with one embodiment.

Referring to the drawings, a system 10 for photoaltering a material 12 is shown in FIG. 1. The system 10 includes, but is not necessarily limited to, a laser 14 capable of generating a pulsed laser beam 18, an energy control module 16 for varying the pulse energy of the pulsed laser beam 18, a scanner 20 operable in response to a control signal, a controller 22 operable to transmit the control signal, and focusing optics 28 for directing the pulsed laser beam 18 from the laser 14 on or within the material 12. The controller 22, such as a processor operating suitable control software, transmits a control signal to control the scanner 20 and/or focusing optics 28 to direct a focal point 30 of the pulsed laser beam along a scan pattern on the surface of the material or in the material 12 (e.g., at a sub-surface depth). To impart at least a portion of this control, software, firmware, or the like, operated by the controller 22 can be used to command the actions and placement of the scanner via a motion control system, such as a closed-loop proportional integral derivative (PID) control system.

In one embodiment, the scanner 20 moves the focal point of the pulsed laser beam 18 in increments through a desired scan pattern as controlled by the controller 22. The step rate at which the focal point is moved is referred to herein as the scan rate. For example, the scanner 20 can operate at scan rates between about 10 kHz and about 400 kHz, or at any other desired scan rate, and may selectively switch between one or more substantially constant scan rates. Further details of laser scanners are known in the art, such as described, for example, in U.S. Pat. No. 5,549,632, the entire disclosure of which is incorporated herein by reference. In some embodiments, the pulsed laser beam 18 may be scanned at a rate between about 1 kHz and about 1 GHz, with a pulse energy of about 800 nJ/pulse, with a pulse width between about 300 picoseconds and about 10 femtoseconds, and/or at a wavelength between about 400 nm to about 3000 nm. The system 10 may also operate with a pulsed laser beam 18 at other pulse energies. In this embodiment, the system 10 further includes a beam splitter 26 and a detector 24 coupled to the controller 22 for a feedback control mechanism of the pulsed laser beam 18.

To provide the pulsed laser beam, a chirped pulse laser amplification system, such as described in U.S. Pat. No. RE37,585, may be used for photoalteration. U.S. Pat. Publication No. 2004/0243111 also describes other methods of photoalteration. Other devices or systems may also be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

Although used to photoalter a variety of materials (e.g., organic, inorganic, or a combination thereof), the system 10 is suitable for ophthalmic applications in one embodiment. In this case, the focusing optics 28 direct the pulsed laser beam 18 toward an eye (e.g., onto a cornea) for plasma mediated (e.g., non-UV) photoablation of superficial tissue, or into the stroma for intrastromal photodisruption of tissue. In this embodiment, the system 10 may also include an applanation lens (not shown) to prepare the cornea for scanning by the pulsed laser beam 18. The system 10 is capable of generating the pulsed laser beam 18 with physical characteristics similar to those of the laser beams generated by a laser system disclosed in U.S. Pat. Nos. 4,764,930, 5,993,438, or the like.

For example, the ophthalmic laser system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue except at the focal point depth of the pulse laser beam 18. The wavelength of the pulsed laser beam 18 is generally in the range of about 3 µm to about 1.9 nm, preferably between about 400 nm to about 3000 nm, and the irradiance of the pulsed laser beam 18 for accomplishing photodisruption of stromal tissues at the focal point is greater than the threshold for optical breakdown of the tissue Although a non-UV, ultrashort pulsed laser beam is described in this embodiment, the pulsed laser beam 18 may have other pulse durations and different wavelengths in other embodiments.

For ophthalmic applications, the scanner 20 may utilize a pair of scanning mirrors or other optics (not shown) to angularly deflect the pulsed laser beam 18 and/or transversely move the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis. In preparing a corneal bed for flap separation, for example, a circular area may be scanned using a scan pattern driven by the scanning mirrors.

The pulsed laser beam 18 photoalters the stromal tissue by scanning the focal point of the pulsed laser beam 18 in a pattern of spots (e.g., based on the scan pattern) for a variety of incisions, the distribution of which is determined by the pulse frequency, the scan rate, and the amount of scan line separation. Generally, higher scan rates, enable shorter procedure times by increasing the rate at which corneal tissue can be photoaltered. For example, the scan rates may be selected from a range between about 30 MHz and about 1 GHz with a pulse width in a range between about 300 picoseconds and about 10 femtoseconds, although other scan rates and pulse widths may be used. While scanning is described using mirrors and focusing objectives to direct the pulsed laser beam in one embodiment, the system 10 may be configured with a moveable laser head to direct the pulsed laser beam at a desired region and along a desired path in another embodiment.

Figure 2:
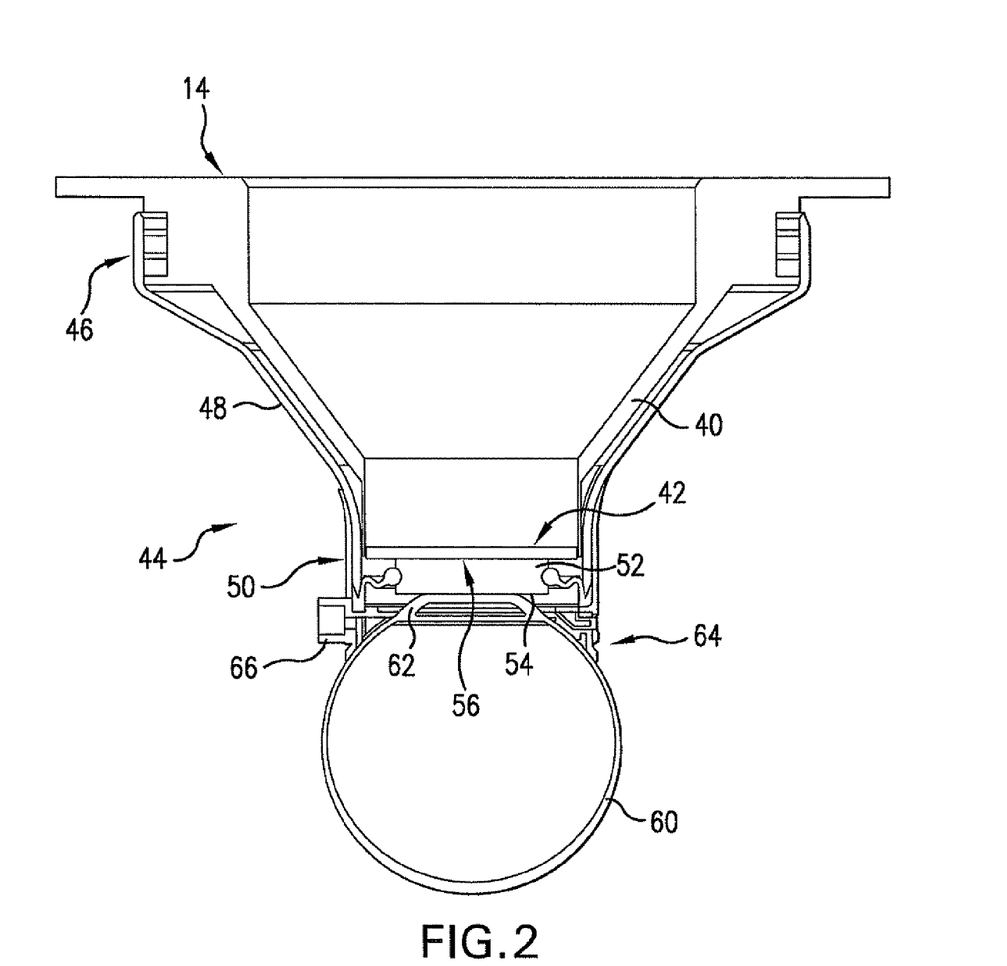
FIG. 2 is a sectional view of a patient interface system incorporating the patient interface device in accordance with one embodiment.

FIG. 2 is a sectional view of a patient interface system 44 incorporating a patient interface device 48 in accordance with one embodiment. The patient interface device 48 couples the laser 14 with the eye 60 and is employed to substantially immobilize the eye during surgery. In this embodiment, a portion of the laser 14 shown in FIG. 1 (e.g., a laser head 40) is coupled to the patient interface device 48. The patient interface device 48 includes a first end 46 for receiving the laser head 40 and a second end 50 having a corneal interface lens 52 for contacting the eye 60. The corneal interface lens 52 has an anterior surface 56 and a posterior surface 54, and may be planar, as shown, or one or both of the surfaces 56, 54 may be curved.

In operation, the first end 46 receives the laser head 40, and an output surface 42 of the laser head 40 contacts the anterior surface 56 of the corneal interface lens 52. The posterior surface 54 contacts the cornea 62 during the surgical procedure and flattens, configures, or otherwise shapes the cornea for the surgical procedure as the posterior surface 54 is applied to the cornea. In one embodiment, the corneal interface lens 52 has a geometrical configuration based upon the shape to which the cornea is to be conformed during the surgical procedure. The corneal interface lens 27 is preferably made of an inexpensive high strength transparent material, such as glass, plastic, or the like, although other transparent materials may be used.

The second end 50 of the patient interface device 48 includes skirt 64 preferably constructed of a soft, pliable material. When placed against the eye 60 as shown, the skirt 64 forms a chamber in combination with the surface of the eye 60. The skirt 23 also includes an arm 66 in fluid connection with the chamber for generating a negative pressure therein and thereby coupling the skirt 23, and thus the patient interface device 11, to the eye 39. A vacuum pump may be used to generate the negative pressure including, by way of example and not limitation, a syringe or any other mechanical device capable of generating a negative pressure. In another embodiment, a suction ring or other attachment device may be used in place of the skirt 64 to couple the second end 50 eye of the patient interface device 48 with the eye 60.

Figure 3:
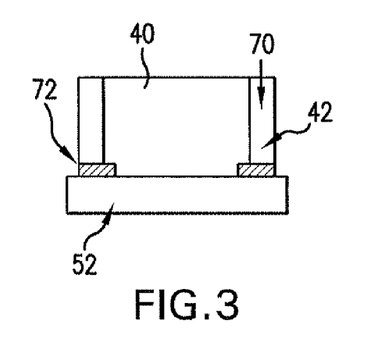
FIG. 3 is a sectional view of the laser head in contact with the corneal interface lens shown in FIG. 2 in accordance with one embodiment.
Figure 4:
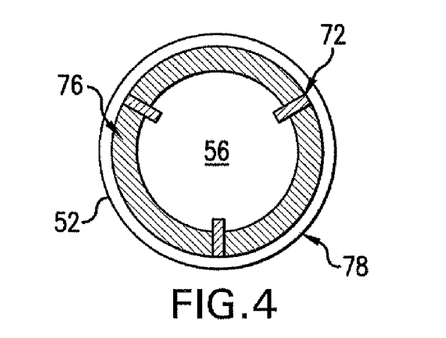
FIG. 4 is a top view of the corneal interface lens shown in FIG. 3 illustrating ohmic contacts overlaying the anterior surface of the corneal interface lens.

The position of the output surface 42 of the laser head 40 may be determined and verified with respect to the anterior surface 56 of the corneal interface lens 52. FIG. 3 is a sectional view of the laser head 40 in contact with the corneal interface lens 52 shown in FIG. 2 in accordance with one embodiment. FIG. 4 is a top view of the corneal interface lens 52 shown in FIG. 3 illustrating ohmic contacts 72 overlaying the anterior surface 56 of the corneal interface lens 52. Referring to FIGS. 1, 3, and 4, the ohmic contacts 72 (e.g., three (3) ohmic contacts) are formed on or integrated with the output surface 42 of the laser head 40 (e.g., coupled to a laser aperture wall 70 of the laser head 40) and coupled to the detector 24. In another embodiment, the detector 24 is integrated with the controller 22. The anterior surface 56 of the corneal interface lens 52 has a periphery 78 with an electrically conductive ring coating 76 (e.g., a metallic ring coating) on the periphery 78. The conductive ring coating 76 may be evaporated onto the periphery 78 or applied to the periphery by other methods.

Figure 5:
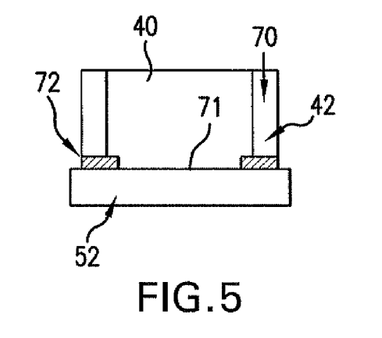
FIG. 5 is a sectional view of the laser head in contact with the corneal interface lens shown in FIG. 2 in accordance with another embodiment.
Figure 6:
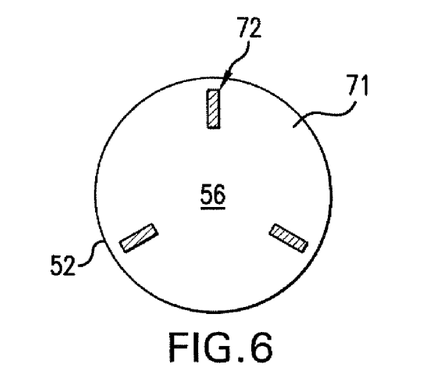
FIG. 6 is a top view of the corneal interface lens shown in FIG. 5 illustrating the ohmic contacts overlaying the anterior surface of the corneal interface lens.

FIG. 5 is a sectional view of the laser head 40 in contact with the interface lens 52 shown in FIG. 2 in accordance with another embodiment. FIG. 6 is a top view of the interface lens shown in FIG. 5 illustrating the ohmic contacts 72 overlaying the anterior surface 56 of the corneal interface lens 52. The number of ohmic contacts 74 (e.g., one or more) may vary for different embodiments, although at least two ohmic contacts are preferred. Additionally, the ohmic contacts 74 are preferably formed outside of the surgical view (e.g., the field of view through the output surface 42). Referring to FIGS. 1, 5, and 6, the ohmic contacts 72 are also formed on or integrated with the output surface 42 of the laser head 40 and coupled to the detector 24. In this embodiment, the anterior surface 56 of the corneal interface lens 52 is coated with a substantially transparent electrically conductive coating 71 (e.g, indium tin oxide).

Referring to FIGS. 1-6, when the output surface 42 of the laser head 40 contacts the corneal interface lens 52, one or more of the ohmic contacts 72 may contact the electrically conductive coating 71 or 76. For example, as part of the docking procedure, the corneal interface lens 52 is brought to contact with the output surface 42 of the laser head 40. The resistance between the ohmic contacts 72 decreases as a result of contact with the electrically conductive coating 71 or 76. The detector 24 senses this resistance change (e.g., a decrease in resistance) among the ohmic contacts 72. Based on predetermined or historical measurements, the controller 22 or detector 24 can compare the resistance change with known resistances to determine the relative position of the output surface 42 with respect to the anterior surface 56 of the corneal interface lens 52.

The controller 22 or detector 24 may further calculate corrections to properly align the output surface 42 with the anterior surface 56 of the corneal interface lens 52. In another embodiment, the controller 22 or detector 24 may simply indicate when the resistance change sufficiently decreases to a threshold resistance indicating the proper alignment of the output surface 42 with the anterior surface 56 of the corneal interface lens 52. Once the output surface 42 is determined to be properly aligned with the anterior surface 56 of the corneal interface lens 52, the laser head 40 may be locked into this position (e.g., by securing the laser head 40 against the patient interface device 48 using an inflatable tube or bladder, or using other methods, to bias the laser head 40 against the first end 46 of the patient interface device 40). In one embodiment, the system 10 automates the coupling/decoupling of the output surface 42 with the anterior surface 56 of the corneal interface lens 52 (e.g., using servo motors or the like) to align the output surface 42 with the anterior surface 56.

Figure 7:
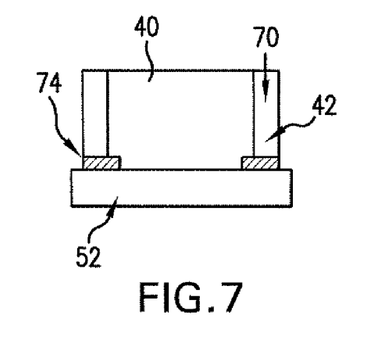
FIG. 7 is a sectional view of the laser head in contact with the corneal interface lens shown in FIG. 2 in accordance with another embodiment.
Figure 8:
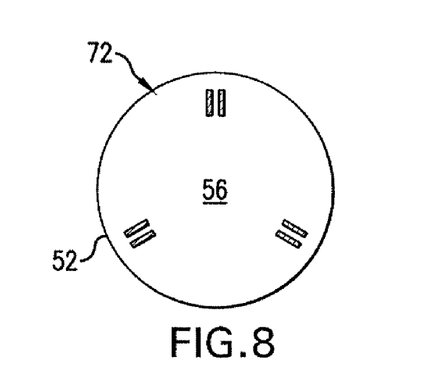
FIG. 8 is a top view of the corneal interface lens shown in FIG. 7 illustrating capacitive contacts overlaying the anterior surface of the corneal interface lens.

FIG. 7 is a sectional view of the laser head 40 in contact with an interface lens 52 shown in FIG. 2 in accordance with another embodiment. FIG. 8 is a top view of the corneal interface lens 52 shown in FIG. 7 illustrating capacitive contacts 74 (e.g., three (3) pairs of capacitive contacts) overlaying the anterior surface 56 of the corneal interface lens 52. The number of capacitive contacts (e.g., one or more) may vary for different embodiments, although at least two capacitive contacts are preferred. Additionally, the capacitive contact are preferably formed outside of the surgical view (e.g., the field of view of through the output surface 42). Referring to FIGS. 1, 7, and 8, the capacitive contacts 74 are formed on or integrated with the output surface 42 of the laser head 40 (e.g., coupled to a laser aperture wall 70 of the laser head 40) and coupled to the detector 24. The capacitive contacts 74 can be formed on the periphery of the output surface 42 of the laser head using lithographic methods or other methods and can be formed to a sufficiently small size for positioning precisions of less than about 10 μm. The corneal interface lens 52 is made of a transparent dielectric material (e.g., glass), which has a dielectric constant different from air. As the output surface 42 is brought into proximity with the corneal interface lens 52, a capacitance associated with the capacitive contacts 74 changes as a result of the presence of the dielectric material. In this embodiment, the anterior surface 56 of the corneal interface lens 52 lacks the conductive coating 71 or 76.

Figure 9:
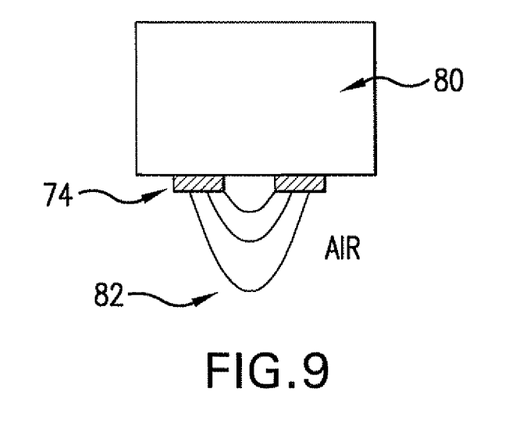
FIG. 9 is a sectional view of uncoupled capacitive contacts.
Figure 10:
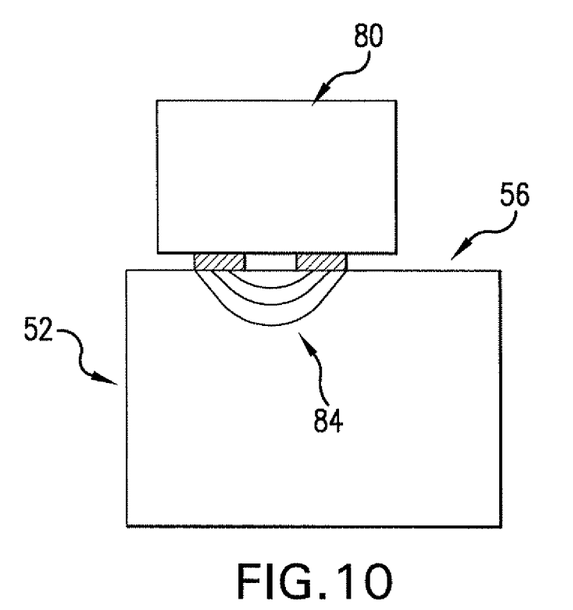
FIG. 10 is a sectional view of the capacitive contacts shown in FIG. 9 in contact with an interface lens.

FIG. 9 is a sectional view of uncoupled capacitive contacts 74. FIG. 10 is a sectional view of the capacitive contacts 74 shown in FIG. 9 in contact with an interface lens, such as the corneal interface lens 52 shown in FIG. 7. A capacitance sensor 80 is coupled with the capacitive contacts 74 and may be integrated with the detector 24 shown in FIG. 1. FIGS. 9 and 10 illustrate a capacitance change (e.g., a decrease in capacitance) of the capacitive contacts 74 as the output capacitive contacts 74 contact the corneal interface lens 52. The controller 22 or detector 24 senses this capacitance change among the capacitive contacts 74. Based on pre-determined or historical measurements, the controller 22 or detector 24 can compare the capacitance change with known capacitances to determine the relative position of the output surface 42 with respect to the anterior surface 56 of the corneal interface lens 52.

The controller 22 or detector 24 may further calculate corrections to properly align the output surface 42 with the anterior surface 56 of the corneal interface lens 52. For example, the controller 22 or detector 24 (e.g., via the capacitance sensor 80) may be calibrated to quantitatively measure the position of the corneal interface lens 52 at each of the capacitive contacts 74. The controller 22 may utilize this date in a closed-loop system to correct the position and/or tilt of the output surface 42 with respect to the corneal interface lens 52 (e.g., in a similar closed-loop method such as described in U.S. Pat. Pub. 20070173791, which is incorporated herewith). In another embodiment, the controller 22 or detector 24 may simply indicate when the capacitance change sufficiently decreases to a threshold capacitance indicating the proper alignment of the output surface 42 with the anterior surface 56 of the corneal interface lens 52. Once the output surface 42 is determined to be properly aligned with the anterior surface 56 of the corneal interface lens 52, the laser head 40 may be locked into this position as previously described.

Figure 11:
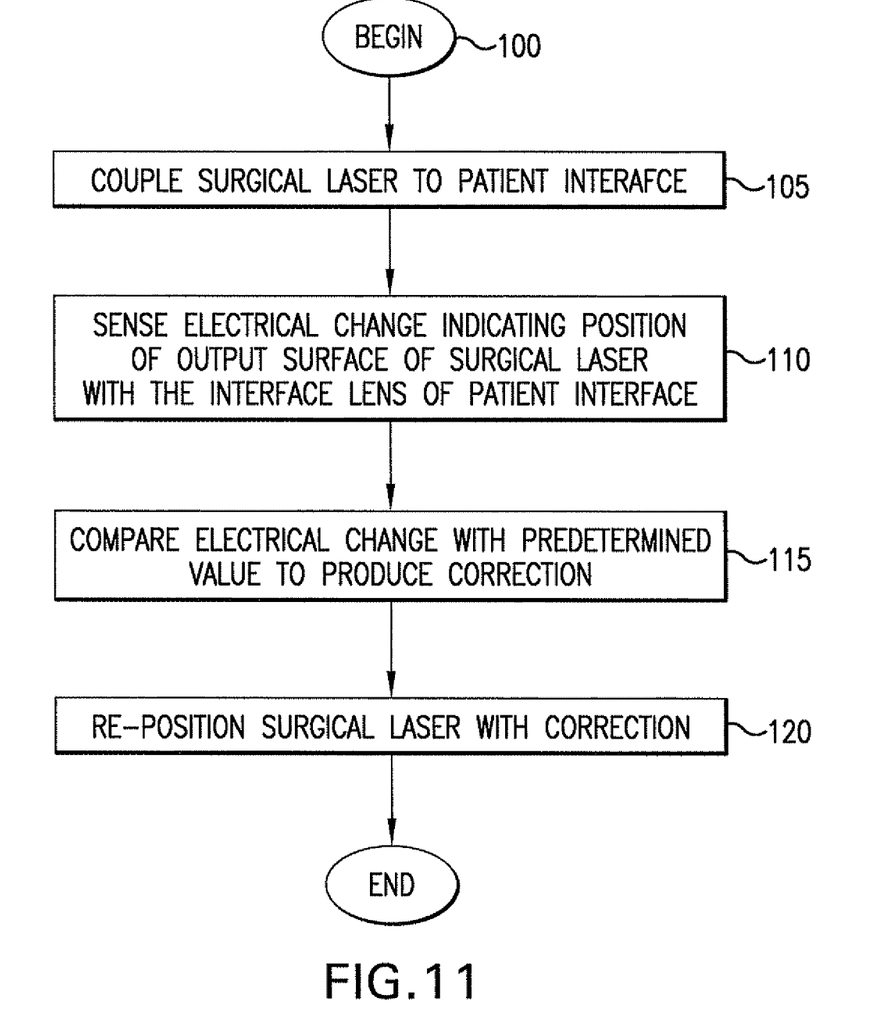
FIG. 11 is a flow diagram of a method for aligning a surgical laser with an eye in accordance with one embodiment.

FIG. 11 is a flow diagram of a method 100 for aligning a surgical laser with an eye in accordance with one embodiment. The surgical laser has a first sensing element coupled to the output surface thereof. The surgical laser is coupled to the patient interface, as indicated at step 105. The patient interface has an interface lens with an anterior surface. Referring to FIG. 2, for example, following coupling of the second end of the patient interface device 48 to the eye 60 (e.g., via the skirt 64), the first end 46 of the patient interface device 48 receives the laser head 40. An electrical change, associated with the first sensing element, is sensed, as indicated at step 110. The electrical change indicates a position of the output surface of the surgical laser with the interface lens (e.g., the position of the output surface 42 with respect to the anterior surface 56 of the corneal interface lens 52). The electrical change is compared with a predetermined value to produce a correction, as indicated at step 115. For example, the first sensing element may be one or more electrodes coupled to the output surface 42, and the electrical change is used to determine a correctable tilt between one or more of these electrodes, and thus the output surface 42, and the anterior surface 56.

In one embodiment, referring to FIGS. 5, 6, and 11, a resistance change among the electrically conductive electrodes 72 (e.g., three (3) ohmic contacts) is determined and indicates contact between one or more of the electrically conductive electrodes 72 with the electrically conductive coating 71. The resistance change may be compared with a predetermined resistance that is associated with all of the electrically conductive electrodes 72 being in contact with the electrically conductive coating 71). The predetermined resistance may be measured using known relative positions and preferably indicates when the surgical laser (e.g., the output surface 42 of the laser head 40) is aligned with the patient interface (e.g., the anterior surface 56 of the corneal interface lens 52). Discrepancies between the resistance change and the predetermined resistance then indicate correctable mis-alignment between the output surface 42 and the anterior surface 56.

In another embodiment, referring to FIGS. 3, 4, and 11, a capacitance change among the capacitive electrodes 74 (e.g., three (3) pairs of capacitive electrodes) is determined and indicates contact between one or more of the capacitive electrodes 74 with the anterior surface 56 of the corneal interface lens 52. The capacitance change may be compared with a predetermined capacitance that is associated with all of the capacitive electrodes 74 being in contact with the anterior surface 56 of the corneal interface lens 52. The predetermined capacitance may be measured using known relative positions and preferably indicates when the surgical laser is aligned with the patient interface device 48. In this embodiment, the corneal interface lens 52 is a dielectric material (e.g., glass, a substantially rigid transparent material, or the like). Discrepancies between the capacitance change and the predetermined capacitance associated with the capacitive electrodes 74 then indicate correctable mis-alignment between the output surface 42 and the anterior surface 56.

After determining the correction, the surgical laser is re-positioned with the correction, as indicated at step 120. The steps 110 through 120 may be repeated until the surgical laser is properly aligned by minimizing or eliminating further corrections to the surgical laser position. For example, the laser head 40 may be re-positioned (e.g, through changes in the x-, y-, and/or z-axes) until the electrical change is determined to be within a predetermined tolerance (e.g., within a threshold resistance or capacitance as determined).

Thus, an ophthalmic patient interface system and a method of interfacing an ophthalmic surgical laser system with an eye are disclosed. While one or more embodiments have been shown and described, it will be apparent to those skilled in the art that more modifications are possible without departing from the inventive concepts herein. The invention, therefore, is not to be restricted except in the spirit of the following claims.

What is claimed is:

1. A surgical system for an eye, the system comprising:
   a laser having an output surface, the output surface comprising a first sensing element; and
   a patient interface having a first end and a second end, the first end of the patient interface configured to couple to the laser, the second end configured to couple to the eye, the patient interface comprising:
   an interface lens having a first surface and a second surface, the first surface of the interface lens configured to contact the eye; and
   a second sensing element coupled to the second surface of the interface lens, the laser operable to couple the output surface with the second surface of the interface lens;
   wherein the first sensing element comprises a plurality of electrically conductive contacts, and
   wherein the second sensing element comprises an electrically conductive coating.

2. The system of claim 1, further comprising a detector coupled to the plurality of electrically conductive contacts, the detector configured to:
   determine when at least one of the plurality of electrically conductive contacts couples to the electrically conductive coating; and
   determine a resistance change between the plurality of electrically conductive contacts, the resistance change indicating a relative position of the output surface of the laser with the second surface of the interface lens.

3. The system of claim 2, further comprising a controller coupled to the detector, the controller configured to:
   compare the resistance change with a predetermined change to produce a correction element; and
   correct the relative position of the output surface using the correction element until the relative position of the output surface matches a predetermined position.

4. The system of claim 1, wherein the electrically conductive coating comprises a transparent conductive oxide.

5. The system of claim 1, wherein the second surface of the interface lens has a periphery, wherein the first sensing element comprises a plurality of electrically conductive contacts, wherein the second sensing element comprises a metallic ring coating on the periphery of the interface, and wherein the system further comprises a detector coupled to the plurality of electrically conductive contacts, the detector configured to:
   determine when at least one of the plurality of electrically conductive contacts couples to the metallic ring coating; and
   determine a resistance change between the plurality of electrically conductive contacts, the resistance change indicating a relative position of the output surface of the laser with the second surface of the interface lens.

6. The system of claim 1, wherein the first sensing element comprises a plurality of capacitive electrodes, and wherein the second sensing element comprises a dielectric.

7. The system of claim 6, further comprising a detector coupled to the plurality of capacitive electrodes, the detector configured to:
   determine when at least one of the plurality of capacitive electrodes couples to the second surface of the interface lens; and
   determine a capacitance change between the plurality of capacitive electrodes, the capacitance change indicating a relative position of the output surface of the laser with the second surface of the interface lens.

8. The system of claim 7, further comprising a controller coupled to the detector, the controller configured to:
   compare the capacitance change with a predetermined change to produce a correction element; and
   correct the relative position of the output surface using the correction element until the relative position of the output surface matches a predetermined position.

\* \* \* \* \*